(12) United States Patent
Grunwald et al.

(10) Patent No.: US 6,254,543 B1
(45) Date of Patent: *Jul. 3, 2001

(54) ADAPTIVE CANCELLATION OF RING-DOWN ARTIFACT IN IVUS IMAGING

(75) Inventors: Sorin Grunwald, Santa Clara; Tat-Jin Teo, Sunnyvale, both of CA (US)

(73) Assignees: SciMed Life Systems, Inc., Maple Grove, MN (US); Boston Scientific Limited, Barbados (BB)

( * ) Notice: Subject to any disclaimer, the term of this patent is extended or adjusted under 35 U.S.C. 154(b) by 0 days.

This patent is subject to a terminal disclaimer.

(21) Appl. No.: 09/625,149

(22) Filed: Jul. 25, 2000

Related U.S. Application Data

(63) Continuation of application No. 09/165,807, filed on Oct. 2, 1998, now Pat. No. 6,102,862.

(51) Int. Cl.[7] ............................................. A61B 8/00
(52) U.S. Cl. ................................................ 600/447
(58) Field of Search .................................. 600/443–447, 600/462–463, 459, 643

(56) References Cited

U.S. PATENT DOCUMENTS

| | | | |
|---|---|---|---|
| 5,183,048 | 2/1993 | Eberle | 600/463 |
| 5,453,575 | 9/1995 | O'Donnell et al. | 600/463 |
| 5,465,726 | 11/1995 | Dickinson et al. | 600/463 |
| 5,474,074 | 12/1995 | Suorsa et al. | 600/459 |
| 5,601,082 | 2/1997 | Barlow et al. | 600/443 |
| 5,656,763 | 8/1997 | Flax | 73/1.82 |
| 5,921,931 | 7/1999 | O'Donnell et al. | 600/441 |
| 5,935,072 | 8/1999 | Hamilton et al. | 600/447 |
| 5,993,393 | * 11/1999 | Ryan et al. | 600/463 |
| 6,036,650 | 3/2000 | Wu et al. | 600/462 |
| 6,102,862 | 8/2000 | Grunwald et al. | 600/447 |

FOREIGN PATENT DOCUMENTS

| | | |
|---|---|---|
| 0702247A2 | 3/1996 | (EP) . |
| WO 93/00036 | 1/1993 | (WO) . |

* cited by examiner

*Primary Examiner*—Marvin M. Lateef
*Assistant Examiner*—Maulin Patel
(74) *Attorney, Agent, or Firm*—Townsend and Townsend and Crew LLP

(57) ABSTRACT

In an intravascular ultrasonic (IVUS) imaging system ring-down artifact is reduced or eliminated by dynamically enhancing the ring-down over a plurality of scans, determining the ring-down range by keying on a ring-down-to-blood transition characterized by a rapid change from high amplitude to low amplitude echoes, and using a spectral pattern for a single or several A-scans within the ring-down range, using for example an FFT analysis, as the basis of selectively filtering current or subsequent images using the recently computed ring-down pattern.

23 Claims, 5 Drawing Sheets

Fig. 5
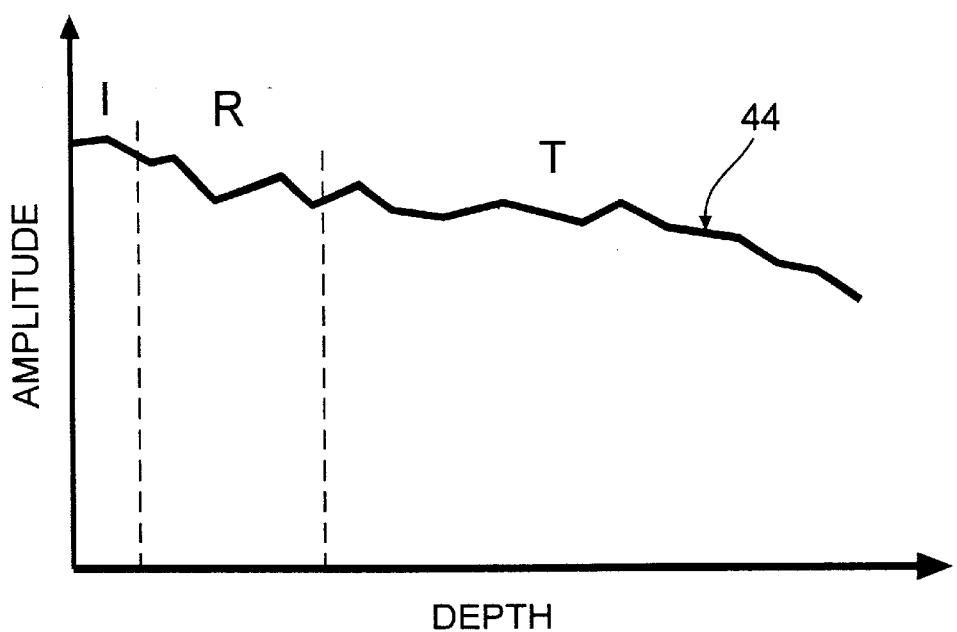
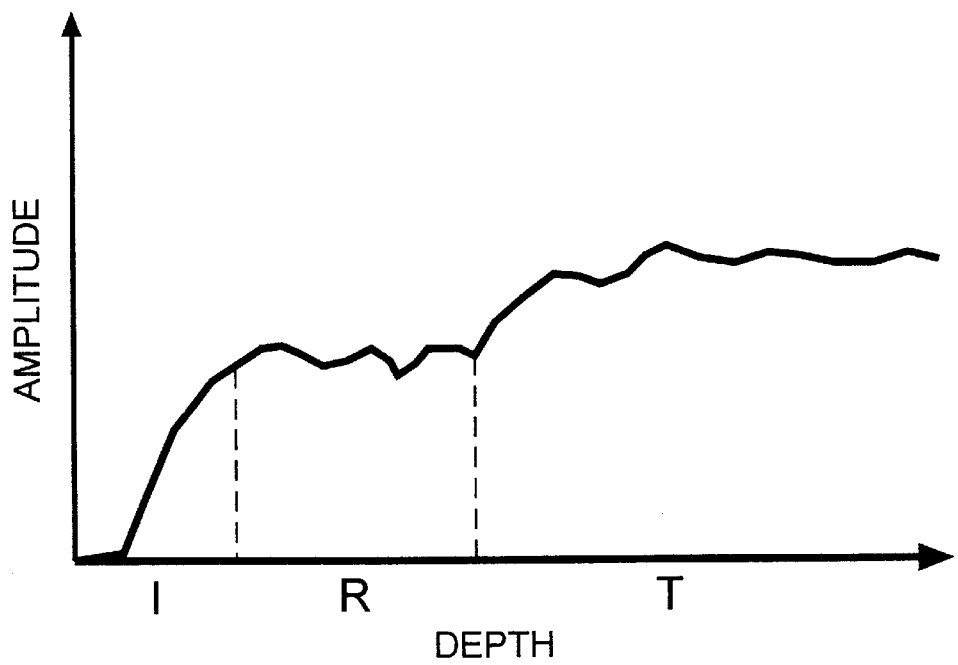
Fig. 6

ADAPTIVE CANCELLATION OF RING-DOWN ARTIFACT IN IVUS IMAGING

This application is a continuation of and claims the benefit of U.S. application Ser. No. 09/165,807, filed Oct. 2, 1998, now U.S. Pat. No. 6,102,862.

BACKGROUND OF THE INVENTION

This invention relates to ultrasonic imaging and more particularly to suppression of spurious artifact signals at ranges close to an excitation source, herein known as ring-down artifact.

Ring-down artifact is caused by transients associated with an exciter which cause interference with informational signals reflected from sources close to the exciter (echo signals). In close-in imaging, such as in intravascular structures, undesired ring-down artifact can impede accurate imaging.

One known mechanism for eliminating ring-down artifact is to gate on the echo signal so that all artifacts are eliminated in the close-in region where ring-down is expected to occur. However, useful echo signals are also eliminated by gating.

Another method described in U.S. Pat. No. 5,601,082, the disclosure of which is herein incorporated by reference, is to generate a reference scan to develop a long-term average and use the reference scan to subtract on all but useful echo signals. However, subtraction of a reference scan may also remove useful echoes having a time constant of the same order of magnitude as the averaged reference scan. Thus subtraction based on a simple reference scan is inadequate to analyze a full range of signal types. What is needed is a more accurate technique for identifying ring-down artifact so it can be separated from legitimate signals.

SUMMARY OF THE INVENTION

According to the invention, in an ultrasonic in-vivo imaging system, ring-down artifact is reduced or eliminated by dynamically enhancing the ring-down over a plurality of scans, and then determining the ring-down range by keying on a ringdown-to-blood transition characterized by a rapid change from high amplitude to low amplitude echoes. A ring-down pattern is computed for a single or several A-scans within the ring-down range, using for example an FFT analysis, and then selectively filtering subsequent images using the recently computed ring-down pattern.

In one exemplary embodiment, the invention provides a method for filtering an in-vivo ultrasonic signal. According to the method, an ultrasonic signal is emitted and a return signal is collected which includes at least an artifact component and a blood component. A transition region in the collected return signal is then identified, with the transition region having the artifact component and the artifact component combined with the blood component. A ring-down pattern in the transition region is then determined based at least in part on the artifact component. Once the ring-down pattern is identified, at least some of (and preferably substantially all of) the artifact component is filtered from the collected return signal based on the ring-down pattern.

The transition region is preferably identified by examining amplitude patterns in the collected return signal. For example, the signal may be analyzed to determine a rapid change from high amplitude to low amplitude. In many cases, the return signal will include a low frequency, high amplitude pattern which is indicative of the ring-down artifact, and a high frequency, low amplitude pattern which is indicative of blood. The point at which such a change is detected is referred to as a transition point and divides the signal into the transition region and a target or blood region.

Optionally, spectral patterns in the collected return signal may also be examined. Use of the spectral patterns can assist in identifying the transition region after the transition point has been identified or approximated.

Conveniently, a catheter is introduced into a body lumen and an ultrasonic source is excited within the catheter to emit the ultrasonic signal. In another aspect, the artifact component is enhanced so that the artifact component is readily identified. This may be done mechanically by repositioning the ultrasonic source. Enhancement may also occur electronically or by software. For example, the emitting and collecting steps may be repeated at different locations to obtain multiple scans. These scans are then convolved to dynamically enhance a pattern of ring-down artifacts as an accumulated ring-down pattern.

In another aspect, the ring-down pattern is stored for use in analyzing subsequent scans. The stored ring-down pattern for is then used for filtering where a ring-down-to blood transition is not found in a subsequent scan. In still another aspect, the step of determining the ring-down pattern comprises obtaining a Fourier transform of the transition region and the blood region of the collected return signal and subtracting the transformed blood region from the transformed transition region.

This invention will be better understood by reference to the following detailed description in connection with the accompanying drawings.

BRIEF DESCRIPTION OF THE DRAWINGS

FIG. 5 is a graph illustrating another scan generated with the ultrasonic source being adjacent tissue.

FIG. 6 is the graph of FIG. 5 having the ring-down pattern of FIG. 3 being filtered out.

DESCRIPTION OF SPECIFIC EMBODIMENTS

The invention provides exemplary systems and methods for suppressing spurious artifact signals at ranges close to an excitation source. Although useful with essentially any type of ultrasonic system, the invention will find its greatest use with ultrasonic imaging elements which are disposed within catheters, and particularly, imaging catheters employed to produce images of the vascular anatomy. As is known in the art, such catheters include an imaging element that is held within a housing. As the imaging element is excited, transients reflected from the housing interfere with the signals reflected from objects within the anatomy, such as blood, vessel walls, and the like. The invention is able to substantially reduce or eliminate the ring-down artifact caused by such transient signals.

Figure 1:
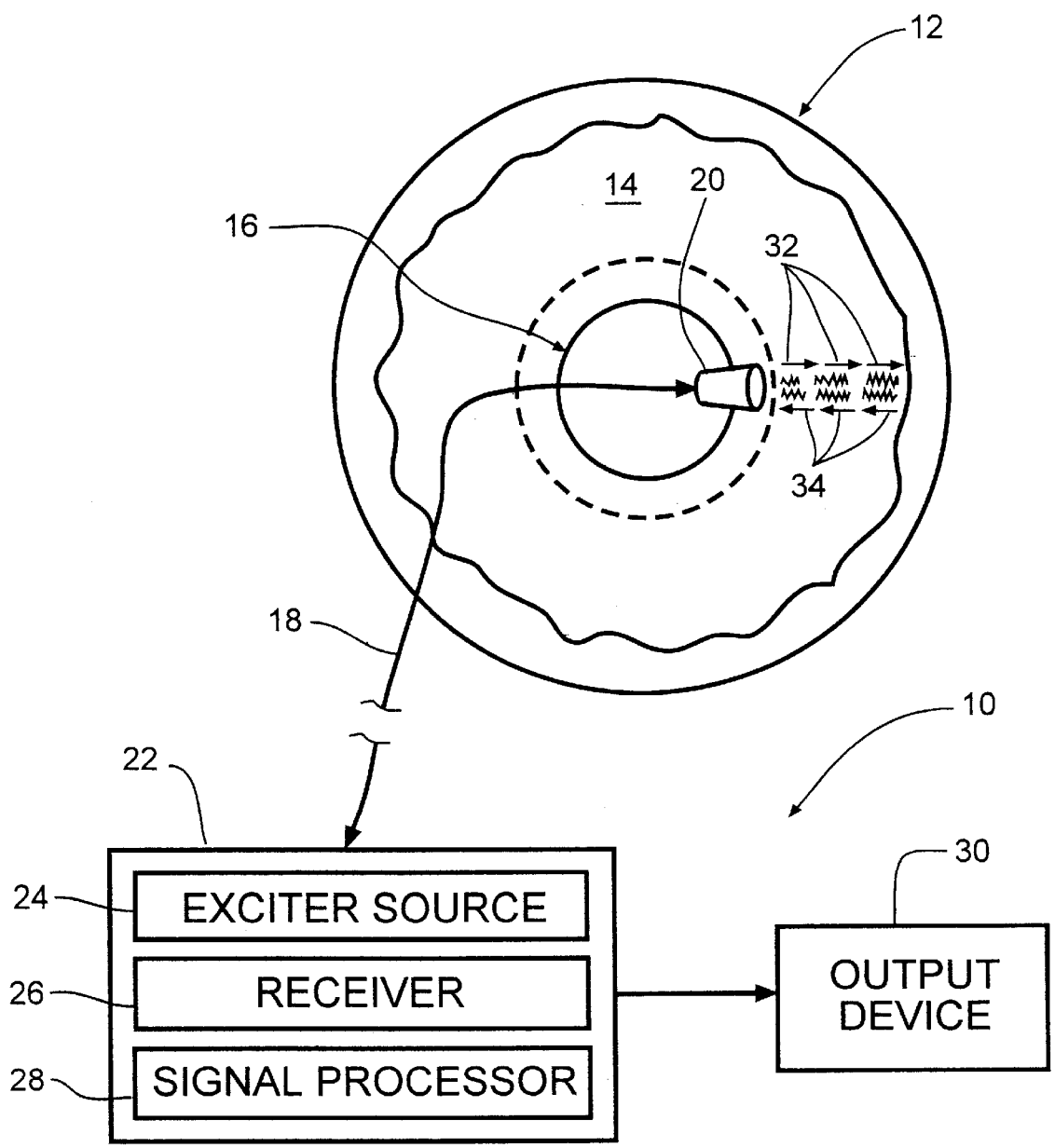
FIG. 1 is a block diagram illustrating a device operative according to the invention for identifying the ring-down region.

Referring to FIG. 1, there is shown basic elements of a simple intravascular ultrasonic (IVUS) imaging system 10 providing imaging of the interior 12 of a vascular subject 14, as shown in an enlarged cross-section. A catheter 16 contains electrical conduits 18 that communicate between a transducer 20 and a console 22 housing an exciter source 24, a receiver 26 a signal processor 28 with associated controls, the output of which is provided to an output device 30, such as a television monitor or a computer display or a combination thereof. The exciter source 24 generates ultrasonic excitation signals 32 of a finite duration that are applied to the transducer 20, which in turn directs those excitation signals 32 in a generally-defined directional beam. Ultrasonic artifact signal 34 is reflected from the interior of the space under observation to be intercepted by the transducer 20, inducing an electrical report which is recovered by the receiver 26 in the console 22. The electrical signals recovered are analyzed by a signal processor 28 operative according to the invention to present an output to the output device 30 which is preferably a reconstructed two-dimensional image of the target cross-section displayed in near real-time. An exemplary medical imaging system that may be used to implement the techniques of the invention is a Galaxy medical imaging system, commercially available from Boston Scientific Corporation.

The transducer 20 may be an array disposed around the skin of the catheter 16, or a single transducer or transducer set which might rotate around the skin of the catheter. As is known in the art, the signal which is emitted from the transducer is referred to as an A-scan. The detected signal along any axis can be reconstructed as the sum of the echo and ring-down artifact which is an amplitude as a function of time.

Figure 2:
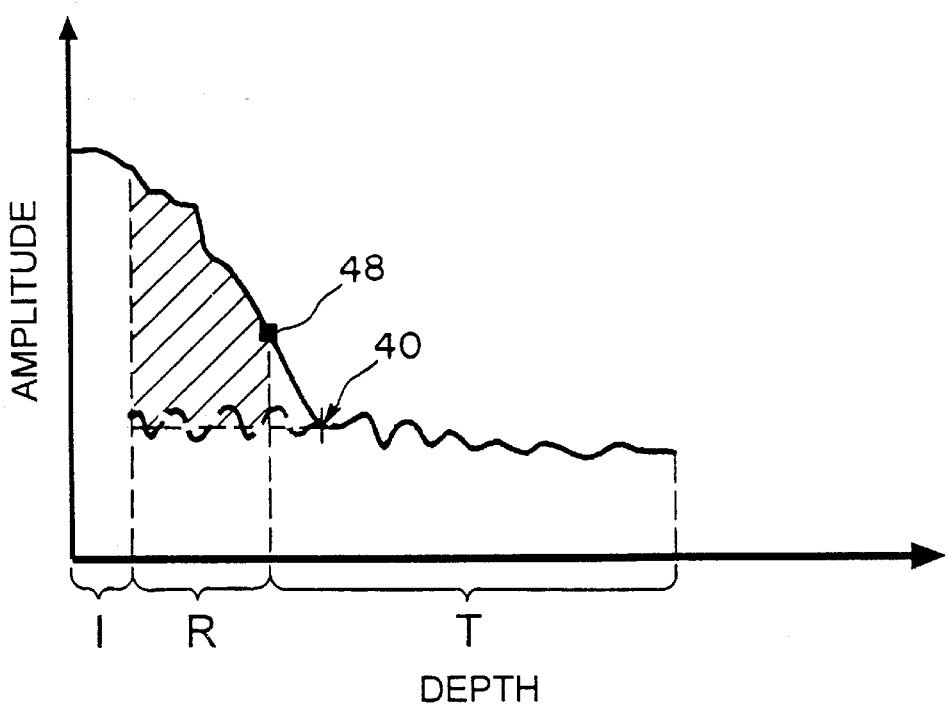
FIG. 2 is a graph illustrating a scan having a ring-down artifact region a target region and a transition region between the artifact region and the target region.
Figure 3:
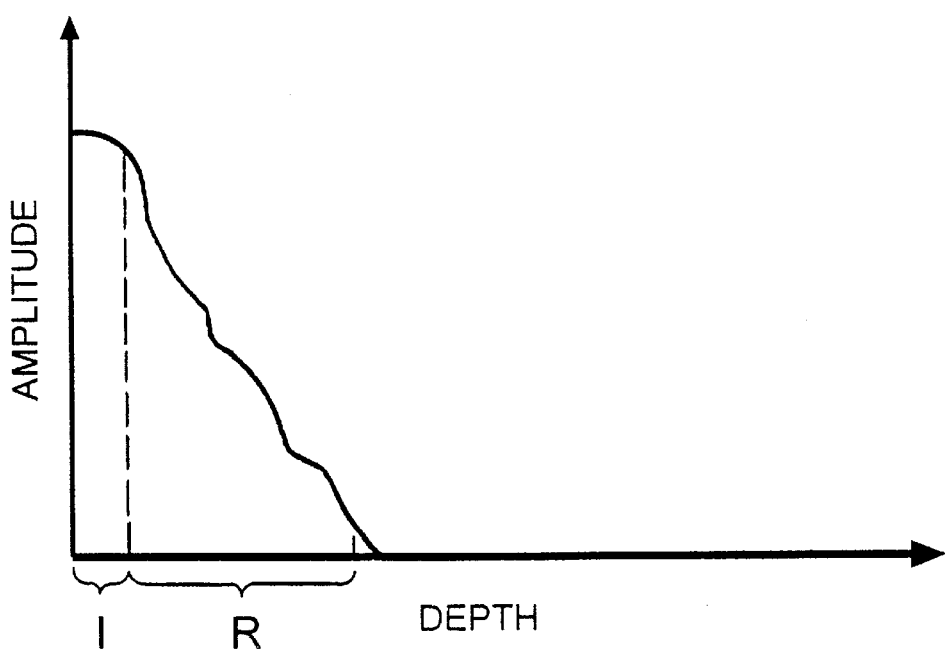
FIG. 3 is the graph of FIG. 2 showing a ring-down pattern in the transition region.
Figure 4:
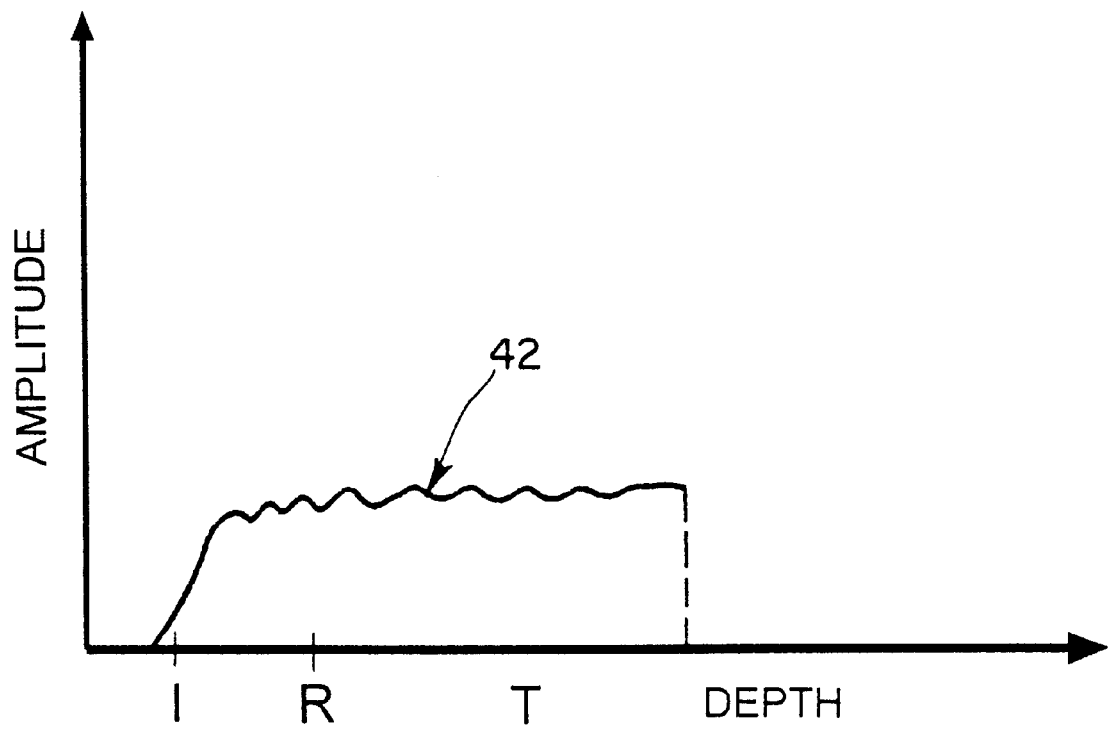
FIG. 4 is the graph of FIG. 2 with the ring-down pattern filtered out.

FIG. 2 is a graph of a trace 40, in this case a convoluted A-scan, and includes both ring-down artifact and echo signal. Such a scan is typical of a scan produced when the transducer is separated from a target region (such as plaque) by blood. The segment I of trace 40 represents pure ring-down. The segment R of trace 40 represents the portion of the overlap of contribution of echo and ring-down, that is, the region where echo begins before the transducer 20 settles. The combination of segments I and R are referred to as the transition region. The segment T is the pure echo without ring-down of the target, which in this case is blood. According to the invention the ring-down contribution or pattern is determined as shown in FIG. 3, then its contribution is subtracted from the composite echo signal in order to yield a more accurate image of the target area as shown in FIG. 4.

The ring-down artifact may be characterized in the time domain and/or the time domain across consecutive scans: several sequential scans are convolved or otherwise averaged together to determine the nature of any repetitive artifacts while canceling any short-term artifacts. The resultant convoluted ring-down pattern (see FIG. 3) is subtracted from the current scan report to yield a scan report 42 with ring-down effectively eliminated, as shown in FIG. 4.

The computation of the ring-down pattern is made for scans for which the following assumption holds: along the A-scan axis, tissue does not intervene between the transducer and the blood region nearest the transducer, such as for example, in FIG. 2. Within that range, it is assumed that only ring-down and blood echoes are present. The typical transition from ring-down to blood echo can be identified by the distinction between signals produced by ring-down and produced by blood. As shown in FIG. 2, the signals produced by ring-down are high amplitude oscillations of relatively low frequency. The signals produced by blood are of low amplitude and high frequency. The ring-down contribution is represented by the crossed hatched area in FIG. 2.

In a system where the target is located abutting the excitation source, the ring-down signal may detrimentally overload the finite, lower-amplitude echo from the target region. With such scans, the previous assumption does not hold because tissue exists near the transducer. As such, a previously computed and stored ring-down pattern (such as the pattern of FIG. 3) is used for selective filtering.

FIG. 5 is a graph of a trace 44 where the transducer is adjacent tissue. To filter the ring-down artifact, the pattern of FIG. 3, which was previously computed, is used for selective filtering. The result is illustrated in FIG. 6 which includes only the signal of the target.

Figure 7:
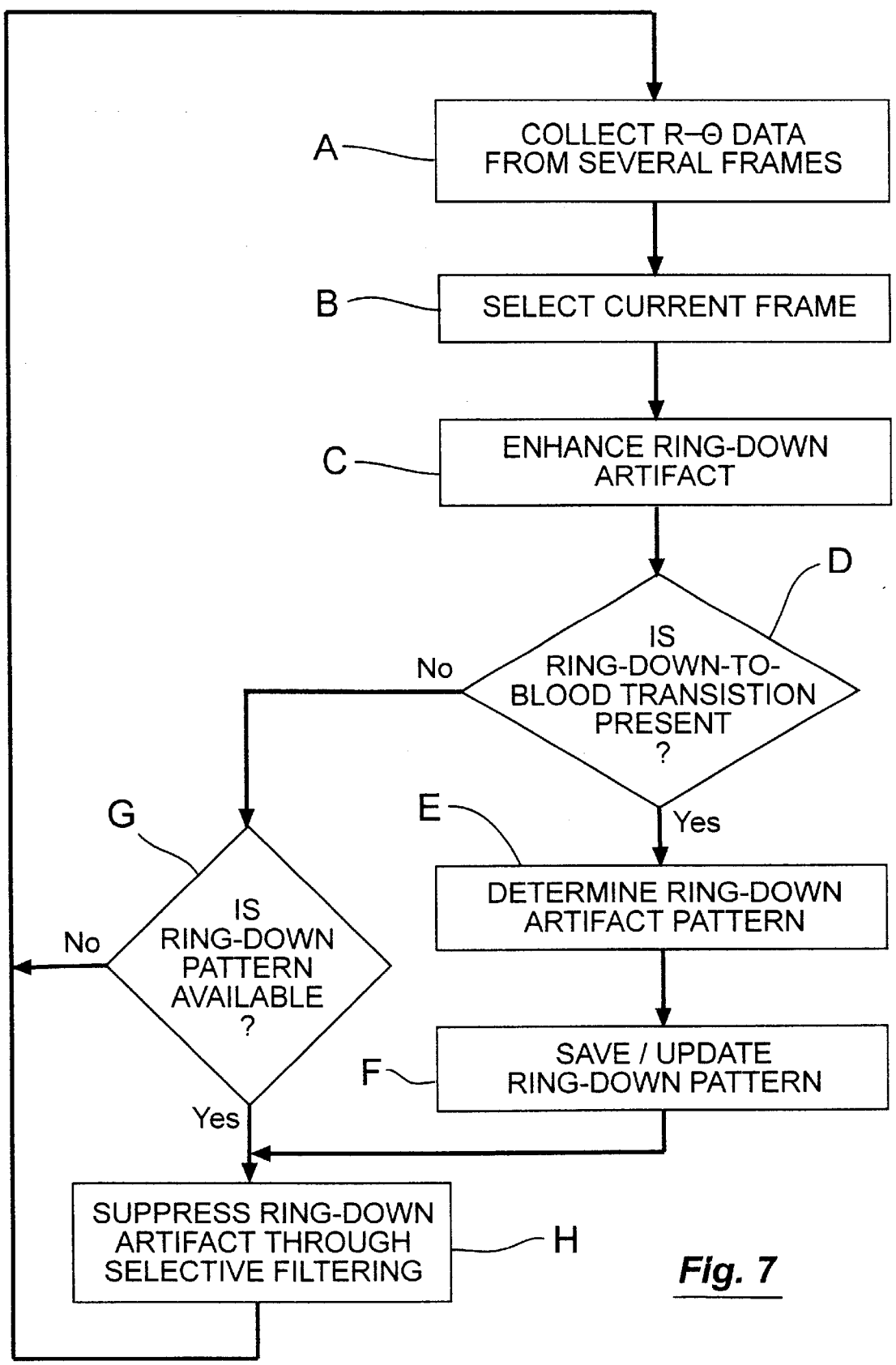
FIG. 7 is a flow chart of the steps according to the inventive method.

Referring to FIG. 7, there is shown a flow chart of a signal processing technique according to the invention. First, the data on a plurality of frames of R-θ data is collected (Step A), and the latest frame is preferably selected as the current frame for processing (Step B). Optionally, the ring-down artifact may be enhanced so it can be more easily characterized (Step C). This may be done mechanically by repositioning the transducer to zero tilt, whereas a slight tilt is normally preferred to suppress such artifact. Enhancement may also be done electronically or by software by the process of convolving several sequential A-scans.

Once the A-scan has been recovered for a frame, the A-scan is inspected to determine the presence of the transition region of ring-down to blood (Step D). This can be an iterative process of examining the time domain signal searching for the boundary between rapid high-amplitude transitions and low-amplitude transitions. The transition between the transition region and the blood region is referred to as a transition point, such as point 48 on FIG. 2.

In some cases, such an amplitude analysis may serve only as a first approximation of the transition point. If so, a second processes may be employed to further define the transition point. For example, the estimated target point may be varied and a fast Fourier transform may be performed on the target region T and on the transition region I and R (see FIG. 2) to covert the time-domain data to frequency-domain data for each variation. This process may be repeated until consistent results are obtained.

Having found the transition point (and thus the transition region), the ring-down artifact pattern in the transition region is computed (Step E). This may be done dynamically by computing the ring-down pattern for one A-scan within the ring-down range. A straightforward fast Fourier transform (FFT) of the transition region and the target region may be used for frequency domain analysis. Such an FFT computation can be performed periodically during real-time imaging for each individual A-scan following other filtering processes, such as blood speckle reduction. Once the FFT values are obtained for the transition region and the target region, a weighted subtraction is performed to. selectively filter out the ring down pattern (such as is shown in FIG. 3). The ring down pattern is preferably saved, and the filtered data is converted back to the time domain to produce the signal shown in FIG. 4.

The ring-down pattern is preferably saved and/or updated for use in the cases where a ring-down-to-blood transition is lacking, e.g., where there is tissue residing next to the transducer (Step F) as shown, for example, in FIG. 5. If there is no ring-down-to-blood transition present, the system checks to see if there is already a ring-down pattern available or previously stored (Step G). If not, the process begins again (Step A) until a pattern emerges, e.g., after a ring-down-to-blood transition is found. Finally, in A-scans having clear ring-down-to-blood transition regions, ring-down artifact is suppressed by a selective filtering, i.e., by subtraction of the ring-down contribution from the signal, to yield a filtered image (Step H). As previously noted, under conditions where a clear transition is lacking, ring-down contribution can be subtracted by using the last known ring-down pattern.

The invention has now been explained with respect to specific embodiments. Other embodiments will be apparent to those of ordinary skill in the art. It is therefor not intended that the invention be limited, except as indicated by the appended claims.

What is claimed is:

1. A method for filtering an in-vivo ultrasonic signal, comprising:

emitting an ultrasonic signal to produce a return signal;

collecting the return signal which comprises at least an artifact component and a blood component;

identifying a transition region in the collected return signal using a processor, wherein the transition region includes the artifact component and the artifact component combined with the blood component;

determining a pattern in the transition region based at least in part on the artifact component; and filtering at least some of the artifact component from the collected return signal based on the pattern.

2. The method of claim 1, wherein the identifying step further comprises examining amplitude patterns in the collected return signal.

3. The method of claim 2, further comprising examining spectral patterns in the collected return signal after examining the amplitude patterns.

4. The method of claim 2, wherein the examined patterns in the collected return signal include a low frequency, high amplitude pattern indicative of ring-down artifact, and a high frequency, low amplitude pattern indicative of blood.

5. The method of claim 1, further comprising introducing a catheter into a body lumen and exciting an ultrasonic source within the catheter to emit the ultrasonic signal.

6. The method of claim 1, further comprising enhancing the artifact component so the artifact component is readily identified.

7. The method of claim 1, further comprising repeating the emitting and collecting steps at different locations to obtain multiple scans, and convolving sequential ones of the scans to dynamically enhance a pattern of ring-down artifacts as an accumulated ring-down pattern.

8. The method of claim 1, further comprising:

storing the pattern for use in analyzing subsequent scans; and using the stored pattern for said filtering where a ring-down-to-blood transition is not found in a subsequent scan.

9. The method of claim 1, wherein the step of determining the pattern comprises obtaining a Fourier transform of the transition region and a blood region of the collected return signal and subtracting the transformed blood region from the transformed transition region.

10. A method for filtering an in-vivo ultrasonic imaging system, the method comprising:

exposing a target region to ultrasonic energy to produce a return signal;

collecting the return signal;

identifying a transition region between a ring-down artifact component and a blood component by examining amplitude patterns of the return signal;

determining, from said examining, a ring-down pattern in the transition region; and filtering the ring-down pattern from the return signal.

11. The method according to claim 10, further comprising examining spectral patterns to assist in identifying the transition region.

12. The method according to claim 10, further including enhancing ring-down artifact so the ring-down artifact component is readily characterized.

13. The method according to claim 10, further including:

convolving sequential scans to dynamically enhance a pattern of ring-down artifacts as an accumulated ring-down pattern.

14. The method according to claim 10, wherein a low frequency, high amplitude segment indicates ring-down artifact, and a high frequency, low amplitude segment indicates blood.

15. The method of claim 10, further including:

storing the ring-down pattern for use in analyzing subsequent scans; and using the ring-down pattern for said filtering where a ring-down-to-blood transition is not found in a subsequent scan.

16. The method according to claim 11, wherein said ring-down characterizing step includes obtaining a Fourier transform to yield said spectral patterns.

17. An apparatus for suppressing ring-down artifact in an in-vivo ultrasonic imaging system comprising:

an exciter to expose a target region to ultrasonic energy;

a receiver that is adapted to receive a reflected signal;

means for identifying a transition region between a ring-down artifact region and a blood region of the reflected signal, said identifying means including means for examining amplitude patterns;

means for determining, from said examining, a ring-down pattern in the transition region; and a filter to filter artifact information based on the ring-down pattern.

18. The apparatus according to claim 17, wherein the exciter is further configured to enhance the ring-down artifact so the ring-down artifact is readily characterized.

19. The apparatus according to claim 17, wherein the ultrasonic energy comprises a scan, and further including:

means for convolving sequential scans of the ultrasonic energy to dynamically enhance a pattern of ring-down artifacts as an accumulated ring-down pattern;

means for storing the accumulated ring-down pattern for use in analyzing subsequent scans; and means for using the accumulated ring-down pattern for said filtering where a ring-down-to-blood transition is not found.

20. The apparatus according to claim 17, further comprising means for assisting in the identification of the transition region by examining spectral patterns.

21. The apparatus according to claim 20, wherein said ring-down determining means includes means for obtaining a Fourier transform to yield said spectral patterns.

22. An ultrasonic imaging system comprising:

a processor;

a memory to store ultrasonic imaging data, including a return signal which includes at least an artifact component and a blood component;

code to identify a transition region in the return signal, wherein the transition region includes the artifact component and the artifact component combined with the blood component;

code to determine a ring-down pattern in the transition region based at least in part on the artifact component; and code to filter at least some of the artifact component from the collected return signal based on the ring-down pattern.

23. A system as in claim 22, further comprising a catheter having an ultrasonic element to produce an ultrasonic signal and the collect the return signal.

* * * * *